United States Patent
Braun et al.

[11] 3,932,411
[45] Jan. 13, 1976

[54] 3,4-DIHYDRO-2H-NAPHTHALENE-1-ONE-5-OXYPROPYL-PIPERAZINE COMPOUNDS

[75] Inventors: Franz Braun, Rimbach; Max Thiel, Mannheim; Kurt Stach, Mannheim-Waldhof; Egon Roesch; Androniki Roesch, both of Mannheim am Oberen Luisenpark, all of Germany

[73] Assignee: Boehringer Mannheim G.m.b.H., Mannheim, Germany

[22] Filed: June 25, 1974

[21] Appl. No.: 482,957

[30] Foreign Application Priority Data
July 12, 1973 Germany............................ 2335432

[52] U.S. Cl............................ 260/268 BC; 424/250
[51] Int. Cl.² ....................................... C07D 241/04
[58] Field of Search ............................... 260/268 BC

[56] References Cited
UNITED STATES PATENTS

| | | | |
|---|---|---|---|
| 3,652,557 | 3/1972 | Beyerle et al................ | 260/268 BC |
| 3,668,206 | 6/1972 | Narayanan et al. .......... | 260/268 BC |
| 3,673,238 | 6/1972 | Elporn et al................. | 260/268 BC |
| 3,810,898 | 5/1974 | Witte et al................... | 260/268 BC |

*Primary Examiner*—Richard J. Gallagher
*Attorney, Agent, or Firm*—Burgess, Dinklage & Sprung

[57] ABSTRACT

New 3,4-dihydro-2H-naphthalene-1-one-5-oxypropyl-piperazine derivatives of the formula:

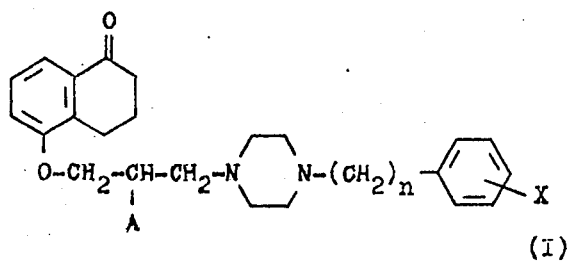

(I)

wherein
A is hydrogen or hydroxyl;
X is hydrogen, halogen, alkyl or alkoxy; and
n is 0, 1 or 2;
and the pharmacologically compatible salts thereof; are outstandingly effective in blood pressure depressing and tranquilizing or sedative therapy; further, these compounds have antioedematous action and reduce capillary permeability.

14 Claims, No Drawings

3,4-DIHYDRO-2H-NAPHTHALENE-1-ONE-5-OXY-PROPYL-PIPERAZINE COMPOUNDS

The present invention is concerned with novel 3,4-dihydro-2H-naphthalene-1-one-5-oxypropyl-piperazine compounds and with therapeutic compositions containing them.

The new 3,4-dihydro-2H-naphthalene-1-one-5-oxypropyl-piperazine compounds according to the present invention are compounds of the formula:

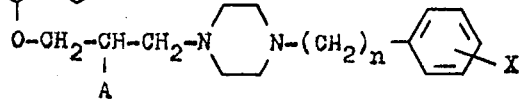

wherein
A is hydrogen or hydroxyl;
X is hydrogen, halogen, alkyl or alkoxy; and
n is 0, 1 or 2;
and the pharmacologically compatible salts thereof.

When A in the compounds of general formula (I) according to the present invention is a hydroxyl group, then the present invention is also concerned with the normally obtained racemic mixtures, as well as with the pure L- and D-enantiomers and the salts thereof.

The new compounds (I) possess outstanding blood pressure-sinking and thus anti-hypertensive properties. We have found that the new compounds have an anti-oedematous action and reduce capillary permeability. They can suppress the liberation and action of histamine and serotonin and thus also have an anti-inflammatory and anti-allergic activity. The substances inhibit the secondary conditioned reactions in rats, without reducing the muscle tone. From this aspect, an action similar to that of chloropromazine on the central nervous system is to be expected, i.e. tranquilizing or sedative properties.

The alkyl and alkoxy radicals in the above formula (I) preferably contain up to 3 carbon atoms.

The new compounds of formula (I) according to the present invention can be prepared, for example, by one of the following methods:

a. reaction of compounds of the formula:

$$Y-CH_2-\underset{A}{CH}-CH_2-Z \qquad (II)$$

wherein Y and Z represent reactive groups, which can be the same or different, and A has the same meaning as above or A and Z together can also represent an oxygen atom, with 5-hydroxy-1-oxotetraline or a reactive derivative thereof and with a piperazine derivative of the formula:

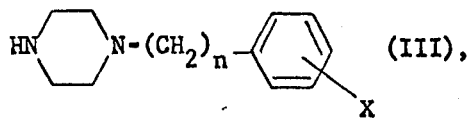

wherein X and n have the same meanings as above, possibly with temporary protection of the group A; or b. when A is a hydroxyl group, reaction of a compound of the formula:

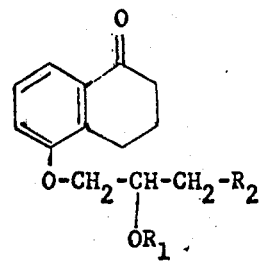

wherein $R_1$ is a hydrogen atom and $R_2$ is a halogen atom or $R_1$ and $R_2$ together also represent a valency bond, or a reactive derivative thereof, with a piperazine derivative of the formula (III) and the reactive derivative converted, if necessary, into a compound of formula (I);

whereafter, if desired, the product obtained is converted into a pharmacologically compatible salt.

As reactive derivatives of 5-hydroxy-1-oxotetraline or of the compounds of formula (IV), there are especially preferred the open and cyclic ketals. After the condensation reaction has taken place, the ketal groupings can be split off with dilute acids.

In the case of process (a), if desired, all three components can be reacted simultaneously. However, it is preferable to carry out the reaction in two stages in which the compounds (II) and (III) are first condensed and the product obtained is subsequently reacted with 5-hydroxy-1-oxotetraline; or also the 5-hydroxy-1-oxotetraline is first reacted with the compound (II) and the reaction product obtained thereafter condensed with a piperazine derivative (III).

The condensation reactions can be carried out in the presence of an acid-binding agent, for example of a tertiary amine, such as triethylamine, or of an appropriate ion exchanger, or of an alkali metal carbonate or bicarbonate, or there can be used the sodium or potassium salt of 5-hydroxy-1-oxotetraline, which is obtained in conventional manner. As solvent, there can be used a lower alcohol, for example isopropanol, or tetrahydrofuran. When A is a hydroxyl group, it is preferable temporarily to block this by means of a protective group which can easily be split off, for example by an acyl radical or a benzyl, triphenylmethyl or tetrahydropyranyl-(2) radical. These protective groups can subsequently be removed again by acidic or alkaline hydrolysis or hydrogenolytically.

Reactive groups Y and Z in the compounds of formula (II) are, in particular, acid residues which can be derived, for example, from hydrohalic acids or from sulfonic acids.

The reaction according to process (b) can be accomplished by mixing together molar amounts of the reaction components and leaving the reaction mixture to stand at ambient temperature; however, the reaction can be accelerated by briefly heating. If desired, a solvent, for example a lower alcohol, can also be added.

As starting materials for process (b), there can be used 5-(2,3-epoxypropyloxy)-tetralone-(1), which is described in German Patent Specification No. 1,948,144.

For the preparation of the salts, the new compounds according to the present invention are reacted with pharmacologically compatible organic or inorganic acids, for example, by hydrochloric acid, sulfuric acid, phosphoric acid, lactic acid, citric acid or an alkyl-sulfonic acid.

The following examples are given for the purpose of illustrating the present invention:

EXAMPLE 1

Preparation of
5-{3-[4-(4-Methylphenyl)-1-piperazinyl]-propoxy}-3,4-dihydro-2H-naphthalene-1-one 55.4 ml (0.4 mol) triethylamine were added to a solution of 35.2 g (0.2 mol) 1-(4-methylphenyl)-piperazine and 31.5 g (0.2 mol) 1-chloro-3-bromopropane in 4 l. ml anhydrous tetrahydrofuran and the reaction mixture then stirred for six hours at 60°–65°C. Thereafter, the crystals which had precipitated out were filtered off with suction and the filtrate was evaporated in a vacuum. There was obtained a quantitative yield of crude 1-(3-chloropropyl)-4-(4-methylphenyl)-piperazine which was purified by rapid distillation at an efficient oil pump vacuum. The yield was 41.23 g (80% of theory); b.p. 147°–150°C/0.05 mm HG; m.p. 34°–36°C.

A solution of 8.1 g (0.05 mol) 5-hydroxy-1-oxotetraline and 3.09 g (0.055 mol) potassium hydroxide in 260 ml isopropanol was boiled under reflux for fifteen minutes. Thereafter, a solution of 13.9 g (0.055 mol) 1-(3-chloropropyl)-4-(4-methylphenyl)-piperazine in 50 ml isopropanol was added thereto and the reaction mixture further heated under reflux for six hours. During this time, a weak current of nitrogen was passed through the apparatus. After cooling and filtering off with suction the precipitated potassium chloride, 15 ml of approximately 7N methanolic hydrochloric acid was stirred into the filtrate. Colorless crystals separated out upon cooling with ice. There were obtained 19.40 g (93.5% of theory) 5-{3-[4-(4-methylphenyl)-1-piperazinyl]-propoxy}-3,4-dihydro-2H-naphthalene-1-one hydrochloride after filtering off with suction. This compound melts at 197°–202°C. After recrystallization from one liter of water, there was obtained the analytically pure substance; yield 13.66 g (66.0% of theory); m.p. 204°–206°C.

The following compounds were obtained in an analogous manner:

5-{3-[4-(2-chlorophenyl)-1-piperazinyl]-propoxy}-3,4-dihydro-2H-naphthalene-1-one from 5-hydroxy-1-oxotetraline and 1-(3-chloropropyl)-4-(2-chlorophenyl)-piperazine; yield 78.0% of theory; m.p. of the hydrochloride (recrystallized from water) 248°–250°C;

5-{3-[4-(4-chlorophenyl)-1-piperzinyl]-propoxy}-3,4-dihydro-2H-naphthalene-1-one from 5-hydroxy-1-oxotetraline and 1-(3-chloropropyl)-4-(4-chlorophenyl)-piperazine; yield 70.0% of theory; the hydrochloride, after recrystallization from 96% ethanol and drying in a vacuum desiccator, still contained 0.55 mol water; m.p. 189°–191°C;

5-{3-[4-(2-methylphenyl)-1-piperazinyl]-propoxy}-3,4-dihydro-2H-naphthalene-1-one from 5-hydroxy-1-oxotetraline and 1-(3-chloropropyl)-4-(2-methylphenyl)-piperazine; yield 73.4% of theory; m.p. of the hydrochloride (recrystallized from water) 243°–245°C;

5-{3-[4-(2-methoxyphenyl)-1-piperazinyl]-propoxy}-3,4-dihydro-2H-naphthalene-1-one from 5-hydroxy-1-oxotetraline and 1-(3-chloropropyl)-4-(2-methoxyphenyl)-piperazine; yield 78.8% of theory; the hydrochloride, after recrystallization from water and drying, contained 0.486 mol water; m.p. 174°–175°C;

5-{3-[4-(4-methoxyphenyl)-1-piperazinyl]-propoxy}-3,4-dihydro-2H-naphthalene-1-one from 5-hydroxy-1-oxotetraline and 1-(3-chloropropyl)-4-(4-methoxyphenyl)-piperazine; yield 84.5% of theory; m.p. of the hydrochloride (recrystallized from ethanol) 191°–192°C;

5-{3-[4-(4-chlorobenzyl)-1-piperazinyl]-propoxy}-3,4-dihydro-2H-naphthalene-1-one from 5-hydroxy-1-oxotetraline and 1-(3-chloropropyl)-4-(4-chlorobenzyl)-piperazine; yield 72.1% of theory; m.p. of the dihydrochloride (recrystallized from 1N hydrochloric acid) 239°C (decomposed);

5-{3-[4-(2-ethylphenyl)-1-piperazinyl]-propoxy}-3,4-dihydro-2H-naphthalene-1-one from 5-hydroxy-1-oxotetraline and 1-(3-chloropropyl)-4-(2-ethylphenyl)-piperazine; yield 70% of theory; m.p. of the hydrochloride (recrystallized from water) 209°–210°C;

5-{3-[4-(4-bromobenzyl)-1-piperazinyl]-propoxy}-3,4-dihydro-2H-naphthalene-1-one From 5-hydroxy-1-oxotetraline and 1-(3-chloropropyl)-4-(4-bromobenzyl)-piperazine; yield 50% of theory; m.p. of the dihydrochloride (recrystallized from 1N hydrochloric acid) 256°–259°C (decomposed);

5-{3-[4-(2-methoxybenzyl)-1-piperazinyl]-propoxy}-3,4-dihydro-2H-naphthalene-1-one from 5-hydroxy-1-oxotetraline and 1-(3-chloropropyl)-4-(2-methoxybenzyl)-piperazine; yield 57.1% of theory; m.p. of the dihydrochloride (recrystallized from 1N hydrochloric acid) 241°–243°C;

5-{3-[4-(2-ethoxybenzyl)-1-piperazinyl]-propoxy}-3,4-dihydro-2H-naphthalene-1-one from 5-hydroxy-1-oxotetraline and 1-(3-chloropropyl)-4-(2-ethoxybenzyl)-piperazine; yield 64.3% of theory; m.p. of the dihydrochloride (recrystallized from ethanol) 223°C;

5-{3-[4-(2-ethoxyphenyl)-1-piperazinyl]-propoxy}-3,4-dihydro-2H-naphthalene-1-one from 5-hydroxy-1-oxotetraline and 1-(3-chloropropyl)-4-(2-ethoxyphenyl)-piperazine; yield 86% of theory; the hydrochloride, after recrystallization from water, contained, after drying, 0.406 mol water; m.p. 196°–197°C.

EXAMPLE 2

Preparation of
5-[3-(4-Phenyl-1-piperazinyl)-propoxy]-3,4-dihydro-2H-naphthalene-1-one 32.43 g (0.2 mol) 5-hydroxy-1-oxotetraline and 120.14 g (0.6 mol) 1,3-dibromopropane were, while stirring, heated to the boil in 200 ml anhydrous isopropanol and thereafter 41.46 g (0.3 mol) pulverized anhydrous potassium carbonate were added thereto over the course of about three hours. Subsequently, the reaction mixture was vigorously stirred for six hours at reflux temperature, then filtered with suction and the filter cake washed out with isopropanol. The filtrate was evaporated in a vacuum and excess 1,3-dibromopropane was substantially stripped off. The oily evaporation residue obtained was taken up in chloroform, the chloroform solution was extracted several times with a dilute aqueous solution of sodium hydroxide, then shaken with water until neutral and dried. After distilling off the chloroform, the oily residue was distilled at oil pump vacuum. Between 145°–155°C/0.05 mm Hg, there were obtained 32.3 g (57.1% of theory) 5-(3-bromopropoxy)-1-oxotetraline, which was then further worked up.

27.64 g (0.2 mol) pulverized anhydrous potassium carbonate were added, while stirring, to a solution of 28.3 g (0.1 mol) 5-(3-bromopropoxy)-1-oxotetraline and 16.22 g (0.1 mol) 1-phenyl-piperazine in 100 ml anhydrous tetrahydrofuran, the reaction mixture was then vigorously stirred for six hours at 60°–65°C, filtered with suction, the filter cake was washed with tetrahydrofuran and the filtrate was evaporated in a vacuum. The oily residue obtained was taken up in 150 ml isopropanol, filtered through charcoal and the solution then mixed, while stirring, with 30 ml approximately 7N methanolic hydrochloric acid. Upon cooling with ice, pale crystals separated out which subsequently, while still moist, were recrystallized from 800 ml 0.1N hydrochloric acid. There were obtained 26.7 g (65.1% of theory) colorless 5-[3-(4-phenyl-1-piperazinyl)-propoxy]-3,4-dihydro-2H-naphthalene-1-one hydrochloride; m.p. 212°–214°C.

EXAMPLE 3

Preparation of 5-{3-[4-(2-chlorophenyl)-1-piperazinyl]-2-hydroxypropoxy}-3,4-dihydro-2H-naphthalene-1-one 8.72 g (0.04 mol) 5-(2,3-epoxypropoxy)-tetral-1-one and 7.84 g (0.04 mol) 1-(2-chlorophenyl)-piperazine were boiled under reflux for two hours in 40 ml absolute ethanol, subsequently cooled with ice and the precipitated crystals were filtered off with suction. There were obtained 14.48 g (87.4% of theory) 5-{3-[4-(2-chlorphenyl)-1-piperazinyl]-2-hydroxypropoxy}-3,4-dihydro-2H-naphthalene-1-one; m.p. 112°–114°C.

For further purification, this base was introduced into 30 ml methanol and mixed with excess 7N methanolic hydrochloric acid. Ether was added thereto and the crystals which precipitated out were filtered off and recrystallized from 650 ml water. There were obtained 14.88 g (82.3% of theory) pure 5-{3-[4-(2-chlorophenyl)-1-piperazinyl]-2-hydroxypropoxy}-3,4-dihydro-2H-naphthalene-1-one hydrochloride which, after drying in a vacuum desiccator, contained 0.511 mol water; m.p. 182°–184°C.

The following compounds were prepared in an analogous manner:

5-{3-[4-(2-methoxyphenyl)-1-piperazinyl]-2-hydroxypropoxy}-3,4-dihydro-2H-naphthalene-1-one
from 5-(2,3-epoxypropoxy)-tetral-1-one and 1-(2-methoxyphenyl)-piperazine; yield 86.5% of theory; m.p. 120°C; after drying in a vacuum desiccator, the hydrochloride contained 0.816 mol water; m.p. 167°–168°C;

5-{3-[4-(2-methylphenyl)-1-piperazinyl]-2-hydroxypropoxy}-3,4-dihydro-2H-naphthalene-1-one
from 5-(2,3-epoxypropoxy)-tetralon-1-one and 1-(2-methylphenyl)-piperazine; yield 55.8% of theory; the hydrochloride, after recrystallizing from water and drying, contained 1 mol water; m.p. 183°–184°C.

EXAMPLE 4

Preparation of 5-{3-[4-(4-Chlorophenyl)-1-piperazinyl]-2-hydroxypropoxy}-3,4-dihydro-2H-naphthalene-1-one 8.72 g (0.04 mol) 5-(2,3-epoxypropoxy)-tetral-1-one and 7.84 g (0.04 mol) 1-(4-chlorophenyl)-piperazine were boiled under reflux for two hours in 40 ml absolute ethanol and thereafter cooled to ambient temperature. The reaction mixture was then acidified with approximately 7N methanolic hydrochloric acid and, after cooling with ice, the precipitated colorless crystals were filtered off with suction. From the mother liquor there was obtained, after the addition of ether, a further crystal fraction. The total yield was 15.88 g (88.1% of theory) 5-{3-[4-(4-chlorophenyl)-1-piperazinyl]-2-hydroxypropoxy}-3,4-dihydro-2H-naphthalene-1-one hydrochloride which, after recrystallization from 85% aqueous ethanol melts at 204°–205°C.

The following compounds were obtained in an analogous manner:

5-{3-[4-(4-methylphenyl)-1-piperazinyl]-2-hydroxypropoxy}-3,4-dihydro-2H-naphthalene-1-one
from 5-(2,3-epoxypropoxy)-tetral-1-one and 1-(4-methylphenyl)-piperazine; yield 92.2% of theory; the dihydrochloride, recrystallized from methanol and tetrahydrofuran, melted, with decomposition, from 235°C;

5-{3-[4-(4-methoxyphenyl)-1-piperazinyl]-2-hydroxypropoxy}-3,4-dihydro-2H-naphthalene-1-one
From 5-(2,3-epoxypropoxy)-tetral-1-one and 1-(4-methoxyphenyl)-piperazine; yield 93.5% of theory; m.p. of the hydrochloride, recrystallized from ethanol; 165°–167°C;

5-[3-(4-phenyl-1-piperazinyl)-2-hydroxypropoxy]-3,4-dihydro-2H-naphthalene-1-one
from 5-(2,3-epoxypropoxy)-tetral-1-one and 1-phenyl-piperazine; yield 90% of theory; the hydrochloride, after recrystallization from water and drying in a vacuum desiccator, contained 0.56 mol water; m.p. 193°–194°C.

EXAMPLE 5

Preparation of 5-{3-[4-(4-Chlorophenyl)-1-piperazinyl[-2-hydroxypropoxy}-3,4-dihydro-2H-naphthalene-1-one 4.92 g (0.025 mol) 1-(4-chlorophenyl)-piperazine in 2.5 ml isopropanol were mixed, while stirring, with 2.30 g (0.025 mol) epichlorohydrin and the reaction mixture further stirred for seventy-five minutes. In the course of 15–20 minutes, the reaction mixture heated up to 70°–80°C and, after 30–40 minutes, 1-(4-chlorophenyl)-4-(3-chloro-2-hydroxypropyl)-piperazine crystallized out which was then filtered off with suction and purified by recrystallization from isopropanol. Without working up the mother liquor, the yield was 3.40 g (47.0% of theory); m.p. 92°–93°C.

A solution of 4.05 g (0.025 mol) 5-hydroxy-1-oxotetraline in 50 ml isopropanol was mixed with 25 ml 1N isopropanolic potassium hydroxide solution and heated under reflux for ten minutes. Thereafter, the crude 1-(4-chlorophenyl)-4-(3-chloro-2-hydroxypropyl)-piperazine prepared above was added thereto after the whole of the reaction mixture had been dissolved by the addition of 20 ml hot isopropanol and the reaction mixture then stirred under reflux for six hours. During this time, a weak current of nitrogen was passed through the apparatus. After cooling and filtering off with suction the precipitated potassium chloride, the filtrate was acidified by stirring with approximately 7N methanolic hydrochloric acid. Upon cooling, colorless crystals separated out which were filtered off and recrystallized from approximately 85% aqueous ethanol. There were obtained 8.92 g (79% of theory) 5-{3-[4-(4-chlorophenyl)-1-piperazinyl]-2-hydroxypropoxy}-3,4-dihydro-2H-naphthalene-1-one; m.p. 204°–205°C.

The new compounds according to the present invention can be admixed with solid or liquid pharmaceutical diluents or carriers and, if desired, also with odoriferous, flavoring and/or coloring materials and then formed, for example, into tablets or dragees or, with the addition of appropriate adjuvants suspended or dissolved in water or in an oil, for example olive oil.

The compounds of the invention constitute potent anti-hypertensive agents. The compounds have proved particularly effective in the treatment of patients with severe or sustained elevation of blood pressure, particularly diastolic pressure. The compounds are suitable for use in almost all forms of fixed and progressive hypertensive disease, including that in which blood pressure is moderately elevated. The compounds have also proved effective in renal hypertension, including hypertension secondary to pyelonephritis, glomerulonephritis and renal amyloidosis. The substances inhibit the secondary conditioned reactions in rats, without reducing the muscle tone, indicating tranquilizing or sedative properties.

The compounds can be administered orally, as pills, tablets, capsules, powders and the like. The preferred form of oral administration is as a tablet containing 1 to 20 mg of active compound.

The compounds can also be administered parenterally. Injection solutions containing 10 mg/ml of the injection solution are preferred.

The dosage schedule is entirely dependent on the condition of the patient, his response to the treatment and whether or not he is ambulatory or hospitalized. The treatment should be begun with small doses (10 mg) and increased gradually depending upon the patient's response. The dosage can be increased at 5 to 7 day intervals until an average daily dose of 1 to 20 mg is reached. Only one dose a day is usually required.

In order to establish the effectiveness of the dihydronaphthalenone compounds of the invention as agents for reducing blood pressure, a series of tests were carried out as follows:

1. Definition of a catalepsy in rats with the method according to Taeschler et al. (Taeschler, M., A. Fanchamps and A. Cerletti: Zur Bedeutung verschiedener pharmakodynamischer Eigenschaften der Phenothiazinderivate fuer ihre klinische Wirksamkeit. Psychiatria et Neurologie 139, 85 – 104(1960)). The method was somewhat modified and carried out as follows: Each of the 4 extremities was put one after the other on a 5 cm high wooden block; if the rat did not pull back the leg within 15 seconds, then one point was given for each extremity. Through graphic interpolation the dosage needed for a two-point rating was determined ($ED_{2\ points}$).

2. A modified open-field-method was employed for the definition of the locomotor depression. In this test, rats which had been treated with the test compounds were compared with rats which had only received solvents. Thirty minutes after the intraperitoneal administering of the substance, the animals were put in pairs (a treated and an untreated animal) into the halves of a box with a surface area of 1 × 1 meter. Two examiners, who did not know which rat had been treated, decided which of the two rats showed less motor activity. If the examiner had to quess, then he gave the animal of his choice one point; if he thought he had detested a difference, two points; if he was sure, three points.

If the choice was correct, these points were marked +, if the choice was incorrect, these points were marked —. When evaluating (calculation of the effective dose), the six possible readings from —3 to +3 were transformed into arbitrary units, —3 being made equal to 0 and +3 to 5. The intermediate values resulted accordingly. From these units and the logarithms of the doses the regression straight line was calculated and the readings of both observers were recorded separately. The $ED_{4\ units}$ indicated the doses which correspond to a median reading of +2 points = 4 units.

3. A catheter was implanted into the A. femoralis of rats for the detection of a blood pressure decreasing effect. The dosage at which the blood pressure decreased by 30 mm Hg was determined 1 – 2 hours after oral application of the substances.

The following compounds were used in the tests:

A — 5-{3-[4-(2-Methylphenyl)-1-piperazinyl]-propyloxy}-3,4-dihydro-2H-naphthalene-1-one;

B — 5-{3-[4-(2-Methoxyphenyl)-1-piperazinyl]-propyloxy}-3,4-dihydro-2H-naphthalene-1-one;

C — 5-{3-[4-(2-Chlorophenyl)-1-piperazinyl]-propyloxy}-3,4-dihydro-2H-naphthalene-1-one;

D — 5-[-3-(4-Phenyl-1-piperazinyl)-propoxy]-3,4-dihydro-2H-naphthalene-1-one; and E — 5-{3-[4-(2-Ethylphenyl)-1-piperazinyl]-propyloxy}-3,4-dihydro-2H-naphthalene-1-one.

The results of the experiment are set out in the Table which follows:

TABLE

Comparison of effective doses (mg/kg) of Chloropromazine and inventive compounds

| | CATALEPSY $ED_{2\ POINTS}$ | LOCOMOTIVE DEPRESSION $ED_{4\ UNITS}$ | BLOOD PRESSURE DECREASE $ED_{-30\ mm\ Hg}$ |
|---|---|---|---|
| Chloropromazine* | 3.5 | 3.1 | 3.0 |
| A | >24.0 | 12.0 | 3.5 |
| B | 10.7 | 3.3 | 3.6 |
| C | >24.0 | 13.0 | 3.7 |
| D | >24.0 | 8.5 | 3.2 |
| E | >24.0 | 9.8 | 3.3 |

*Comparison Compound = 2-chloro-10-(3-dimethylaminopropyl) phenothiazine = MEGAPHEN From the above table it can be seen that the blood pressure decreasing effect of all substances was about the same, whereas the sedative effect (judged by locomotor depression) was somewhat lower than with the comparison substance. To achieve this effect, the new compounds required considerably smaller dosages than the dosages at which rat catalepsy was induced, i.e., the inventive compounds provide a far greater margin of safety with respect to catalepsy than does the comparison substance. Thus, the appearance of extrapyramidal side effects using the inventive compounds in humans can be expected (in contrast to chloropromazine) only when the sedating or blood pressure decreasing dosage is by far exceeded. With chloropromazine, the effective dosage for catalepsy, locomotor depression and blood pressure decrease were about the same.

It will be understood that the specification and examples are illustrative but not limitative of the present invention and that other embodiments within the spirit and scope of the invention will suggest themselves to those skilled in the art.

What is claimed is:

1. 3,4-dihydro-2H-naphthalene-1-one-5-oxypropyl-piperazine compound of the formula

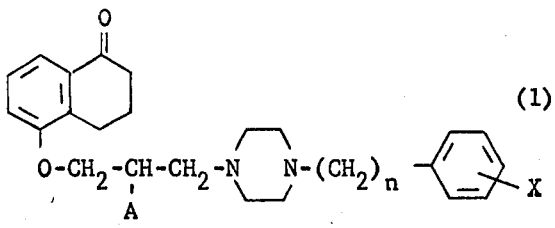

wherein
A is hydrogen or hydroxyl;
X is hydrogen, halogen, alkyl of up to 3 carbon atoms or alkoxy of up to 3 carbon atoms; and
n is 0, 1 or 2;
and the pharmacologically compatible salts thereof.

2. 3,4-Dihydro-2H-naphthalene-1-one-5-oxypropyl-piperazine compound as claimed in claim 1 wherein A is hydrogen.

3. 3,4-Dihydro-2H-naphthalene-1-one-5-oxypropyl-piperazine compound as claimed in claim 1 wherein A is hydroxyl.

4. 3,4-Dihydro-2H-naphthalene-1-one-5-oxypropyl-piperazine compounds as claimed in claim 1 wherein A is hydroxyl and said compounds comprise a racemic mixture.

5. 3,4-Dihydro-2H-naphthalene-1-one-5-oxypropyl-piperazine compound as claimed in claim 1 wherein said compound comprises the L-enantiomer.

6. 3,4-Dihydro-2H-naphthalene-1-one-5-oxypropyl-piperazine compound as claimed in claim 1 wherein said compound comprises the D-enantiomer.

7. 3,4-Dihydro-2H-naphthalene-1-one-5-oxypropyl-piperazine compound as claimed in claim 1 wherein X is hydrogen.

8. 3,4-Dihydro-2H-napthalene-1-one-5-oxypropyl-piperazine compound as claimed in claim 1 wherein X is halogen.

9. 3,4-Dihydro-2H-naphthalene-1-one-5-oxypropyl-piperazine compound as claimed in claim 1 wherein X is alkyl of up to 3 carbon atoms.

10. 3,4-Dihydro-2H-naphthalene-1-one-5-oxypropyl-piperazine compound as claimed in claim 1 wherein X is alkoxy of up to 3 carbon atoms.

11. 3,4-Dihydro-2H-naphthalene-1-one-5-oxypropyl-piperazine compound as claimed in claim 1 wherein $n$ is 0.

12. 3,4-Dihydro-2H-naphthalene-1-one-5-oxypropyl-piperazine compound as claimed in claim 1 wherein $n$ is 1.

13. 3,4-Dihydro-2H-naphthalene-1-one-5-oxypropyl-piperazine compound as claimed in claim 1 wherein $n$ is 2.

14. 3,4-Dihydro-2H-naphthalene-1-one-5-oxypropyl piperazine compound as claimed in claim 1 designated 5-{3-[4-(2-methoxyphenyl)-1-piperazinyl]-propyloxy}-3,4-dihydro-2H-naphthalene-1-one.

* * * * *